US006558332B1

(12) United States Patent
Shimizu

(10) Patent No.: US 6,558,332 B1
(45) Date of Patent: May 6, 2003

(54) ARRAY TYPE ULTRASONIC PROBE AND A METHOD OF MANUFACTURING THE SAME

(75) Inventor: Yasuo Shimizu, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 0 days.

(21) Appl. No.: 10/159,192

(22) Filed: May 30, 2002

(30) Foreign Application Priority Data

May 30, 2001 (JP) ....................................... 2001-163384

(51) Int. Cl.[7] ................................................ A61B 8/00

(52) U.S. Cl. ........................................ 600/459; 600/437

(58) Field of Search ................................. 600/437, 443, 600/459, 460, 444, 447, 445; 367/153; 73/626

(56) References Cited

U.S. PATENT DOCUMENTS 5,497,540 A * 3/1996 Venkataramani et al. ... 600/459
5,810,009 A * 9/1998 Mine et al. ................. 600/459
5,916,169 A * 6/1999 Hanafy et al. .............. 600/459

FOREIGN PATENT DOCUMENTS

JP 11-220795 8/1999

* cited by examiner

*Primary Examiner*—Francis J. Jaworski
*Assistant Examiner*—Maulin Patel
(74) *Attorney, Agent, or Firm*—Katten Muchin Zavis Rosenman

(57) ABSTRACT

An array type ultrasonic probe in which a plurality of rectangular piezoelectric elements is arranged on a backing material is provided. Each piezoelectric element has lower and upper face electrodes and an acoustic matching layer fixedly secured onto the upper face electrode. At one end portion of the piezoelectric element, a first slit is provided for electrically separating the lower face electrode, and at the other end portion of the piezoelectric element, a second slit reaching the piezoelectric element from the acoustic matching layer is provided for separating the upper face electrode. At the opposite ends of the piezoelectric element, the upper and lower face electrodes are electrically connected by conductive adhesive.

13 Claims, 4 Drawing Sheets

ARRAY TYPE ULTRASONIC PROBE AND A METHOD OF MANUFACTURING THE SAME

BACKGROUND OF THE INVENTION

1. Field of the Invention

The present invention relates to an array type ultrasonic probe constructed by arraying a plurality of piezoelectric elements on a backing material, and more particularly it relates to an array type ultrasonic probe having an improved acoustic field characteristic and a method of manufacturing the same.

2. Description of the Related Art

The array type ultrasonic probe is used as a unit for transmitting and receiving an ultrasonic wave in ultrasonic diagnostic equipment for a medical purpose and so on, in order to obtain a tomogram of an examinee, i.e., to obtain a tomogram in vivo. When obtaining a tomogram, a plurality of piezoelectric elements constituting the array type ultrasonic probe are driven by a linear scan method or a sector scan method. In recent years, it has been desired to provide an array type ultrasonic probe having a good acoustic field characteristic of ultrasonic wave, which is transmitted and received, together with an excellent producibility thereof.

FIGS. 1 and 2 are cross-sectional and plan views of an example of a conventional array type ultrasonic probe, respectively.

The array type probe is constructed by arranging a plurality of piezoelectric elements 2, each having upper face electrode 1*a* and lower face electrode 1*b* , on backing material 3. In the illustrated one, a plurality of piezoelectric elements 2, each having a rectangular shape, are arranged in an array in a direction in which the short sides of piezoelectric elements 2 are extended. In a central region of the upper face of each piezoelectric element 2, acoustic matching layer 4 for matching acoustic impedance thereof with an examinee under ultrasonic diagnosis is formed. Also, non-illustrated acoustic lens is formed on acoustic matching layer 4. Further, on the opposite end portions of respective upper faces of piezoelectric elements 2, lead wires 5*a* and 5*b* are connected by soldering for providing joints among the plurality of piezoelectric elements 2, and by lead wires 5*a* and 5*b*, respective upper face electrodes 1*a* are commonly connected together to become earth potential. To lower electrodes 1*b* of respective piezoelectric elements 2, metal foils 6 for the purpose of leading out an electrode are connected in such a manner that they are alternately disposed and connected to one of the opposite ends of the elements 2, and electric driving voltages for respective piezoelectric applied to metal foils 6.

Nevertheless, in the above-described array type probe, ultrasonic wave is radiated from the opposite end portions of piezoelectric elements 2, to which lead wires 5*a* and 5*b* are connected, and the radiated ultrasonic wave interferes with the ultrasonic wave radiated from acoustic matching layer 4 to result in causing a problem such that an adverse affect is provided on the acoustic field characteristic.

Thus, in an array type probe as illustrated in FIG. 3, on one end portion of respective piezoelectric elements 2, lower face electrodes 1*b* are turned up toward the upper face the elements, and on the other end portion of respective piezoelectric elements 2, upper face electrodes 1*a* are turned down toward the lower face. Furthermore, metal foils 6 for earthing are connected to one end portion of the lower faces of respective piezoelectric elements 2, and metal foils 6 for drive signal are connected to the other end portion of the same lower faces. As a result, in the array type probe of this type, respective of the opposite end portions in the longitudinal direction of piezoelectric element 2, in which no acoustic matching layer 4 is arranged, are in a condition where the upper and lower faces thereof are in an identical electric potential, and therefore radiation of the ultrasonic wave is prevented.

In the meantime, in manufacturing piezoelectric element 2, upper electrode 1*a* and lower electrode 1*b* are formed on a piezoelectric body, and thereafter a process is needed to apply a high electric voltage across upper and lower electrodes 1*a* and 1*b* for polarizing the piezoelectric body. In the probe illustrated in FIG. 3, since turn-down portion 1*c* of upper face electrode 1*a* and an end of lower face electrode 1*b* confront one another on the lower face of piezoelectric element 2, during the polarizing process, lest electric field more than necessity might be applied to this confronting portion, it is usually necessary to provide spacing more than a predetermined extent, i.e., an extent equal to or more than the thickness of the piezoelectric body, between turn-down portion 1*c* and the end of lower face electrode 1*b*. Similarly, spacing equal to or larger than a predetermined extent should be provided between turn-up portion 1*d* of lower face electrode 1*b* and an end of upper face electrode la on the upper face of piezoelectric element 2. Thus, a problem has occurred in that an effective length of the central region of piezoelectric element 2, except for the turn-down and turn-up portions, must be made short. Further, since the upper and lower face electrodes provided with turn-down and turn-up portions, respectively, are formed, an effective length of the ultrasonic wave generative face is in turn preset beforehand, and accordingly a problem has occurred in that degree of freedom of design is narrowed.

SUMMARY OF THE INVENTION

An object of the present invention is to provide an array type ultrasonic probe, which enables it to prevent radiation of ultrasonic wave from end portions of piezoelectric elements as well as to extend degree of freedom of design by prolonging an effective length of the piezoelectric element.

Another object of the present invention is to provide a method of manufacturing an array type ultrasonic probe, which enables it to prevent radiation of ultrasonic wave from end portions of piezoelectric elements as well as to extend degree of freedom of design by prolonging an effective length of the piezoelectric element.

The above-described object of the present invention can be achieved by an array type ultrasonic probe, which comprises a backing material; a plurality of piezoelectric elements arranged on and fixedly secured to the backing material, each piezoelectric element having a first end portion, a second end portion opposing the first end portion, a first major face facing the backing material, a second major face, a lower face electrode formed on the first major face, and an upper face electrode formed on the second major face; a first conductive member for electrically connecting the lower face electrode and the upper face electrode at the first end portion; and a second conductive member for electrically connecting the lower face electrode and the upper face electrode at the second end portion; wherein the first major face is formed, along the first end portion, with a first notch portion to thereby electrically separate the lower face electrode, and the second major face is formed, along the second end portion, with a second notch portion to thereby electrically separate the upper face electrode.

The above-described another object of the present invention is achieved by a manufacturing method of an array type ultrasonic probe having a backing material and a plurality of piezoelectric elements arranged on the backing material, which comprises the steps of fixedly securing a piezoelectric plate formed thereon with an upper face electrode and a lower face electrode to the backing material by a first conductive adhesive so that the lower face electrode faces the backing material; forming a first slit running from the upper face electrode to the backing material, relative to a first side of the piezoelectric plate; fixedly securing an acoustic matching layer onto the upper face electrode by a second conductive adhesive while electrically connecting the upper and lower face electrodes by the second adhesive at the first side and a second side of the piezoelectric plate, the second side opposing the first side; forming a second slit running from an upper face of the acoustic matching layer to the piezoelectric plate while separating the upper face electrode, relative to the second side of the piezoelectric plate; and thereafter separating the piezoelectric plate into individual piezoelectric elements.

The above-described another object of the present invention is also achieved by a manufacturing method of an array type ultrasonic probe having a backing material and a plurality of piezoelectric elements arranged on the backing material, which comprises the steps of fixedly securing a piezoelectric plate formed with upper and lower face electrodes together with a first groove separating the lower face electrode on a first side of the piezoelectric plate, and a second groove separating the upper face electrode on a second side of the piezoelectric plate, to the backing material in a manner such that the lower face electrode faces the backing member, by applying insulating adhesive to a central region of the backing material, the second side opposing the first side; applying insulating adhesive to a central region of the upper face electrode and conductive adhesive to the regions of the upper face electrode to thereby fixedly secure an acoustic matching layer onto the upper face electrode while electrically connecting the upper and lower face electrodes by the conductive adhesive at the first and second sides of the piezoelectric plate; and thereafter separating the piezoelectric plate into individual piezoelectric elements.

In the present invention, the lower and upper face electrodes of the piezoelectric plate are separated by the first and second notches provided along the opposite end portions of the piezoelectric plate. The lower and upper face electrodes are connected by the conductive material at each end portion of the piezoelectric plate. Therefore, the opposite end portions of the piezoelectric plate are made to have an identical electrical potential, so that radiation of the ultrasonic wave from the end portions of the piezoelectric elements can be prevented. Also, since the notches are formed after the polarizing processing, width of each notch may be the smallest. Further, the first and second notches may be formed at any arbitrary positions, and accordingly the effective length of the respective piezoelectric elements may be determined in compliance with requested specifications.

DETAILED DESCRIPTION OF THE INVENTION

Figure 1:
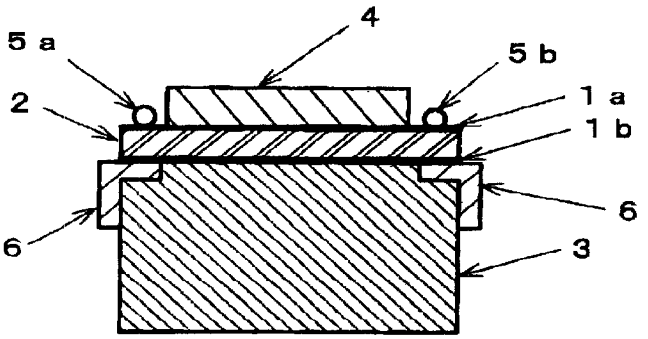
FIG. 1 (PRIOR ART)
FIG. 1 is a cross-sectional view illustrating an example of a conventional array type ultrasonic probe.
Figure 2:
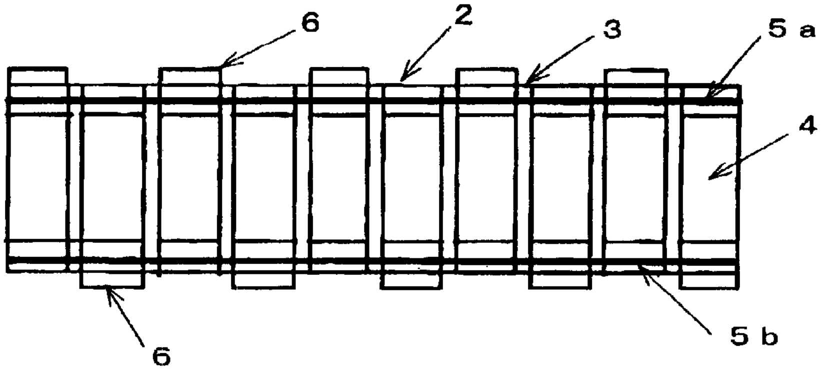
FIG. 2 (PRIOR ART)
FIG. 2 is a plan view of the array type ultrasonic probe shown in FIG. 1.
Figure 3:
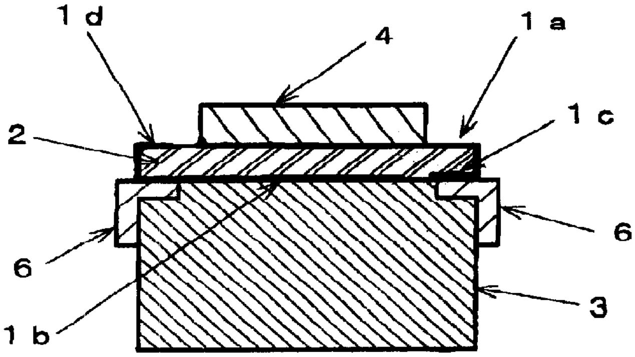
FIG. 3 (PRIOR ART)
FIG. 3 is a cross-sectional view illustrating another example of a conventional array type ultrasonic probe.
Figure 4:
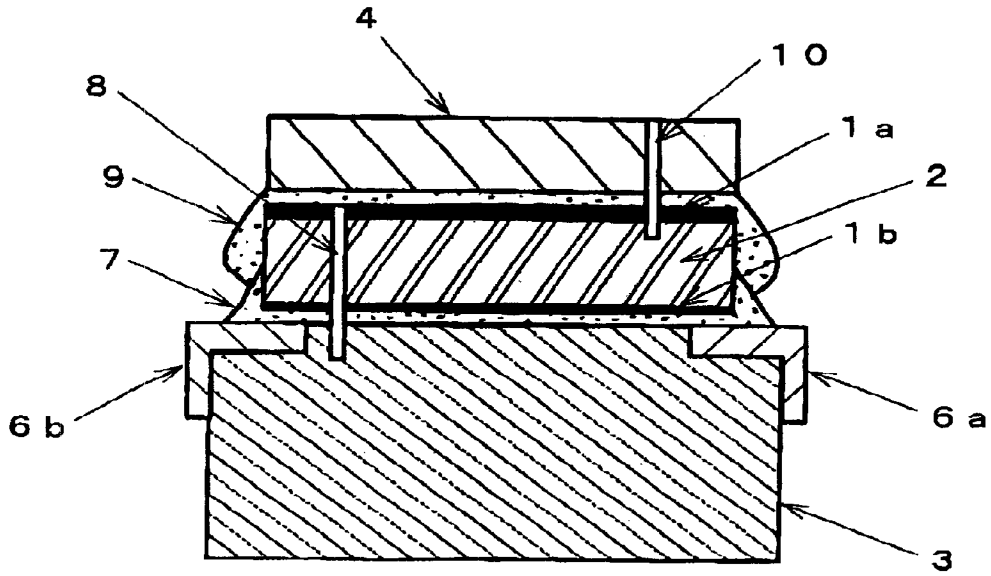
FIG. 4 is a cross-sectional view illustrating an array type ultrasonic probe according to a first embodiment of the present invention.
Figure 5:
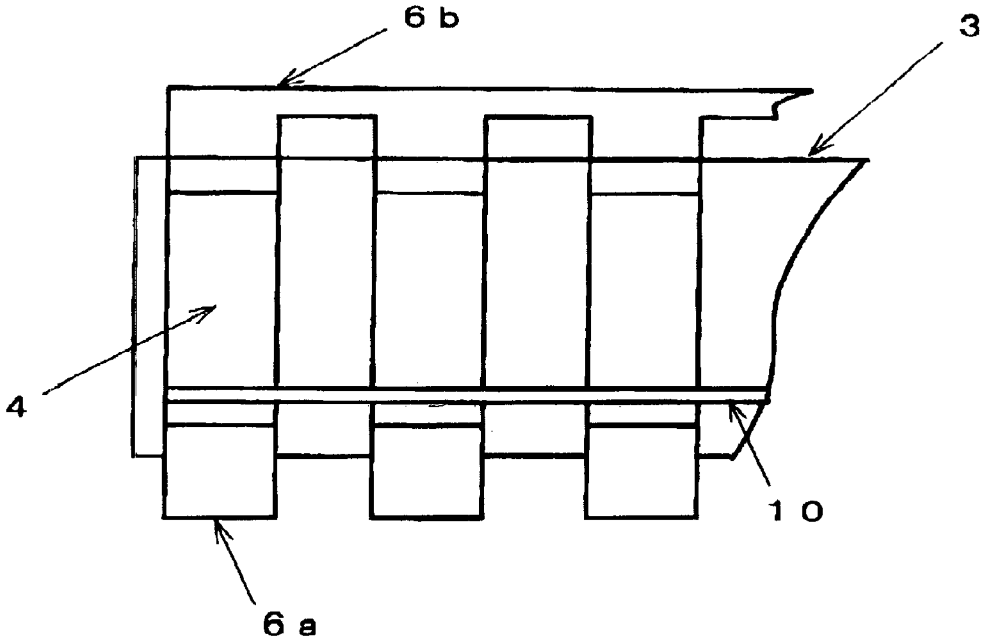
FIG. 5 is a plan view of the ultrasonic probe shown in FIG. 4, illustrating a state where a metallic foil is expanded.

In FIGS. 4 and 5, illustrating an array type ultrasonic probe according to a first embodiment of the present invention, constituting portions designated by the same reference numerals as those in FIGS. 1 and 2 are the same as those in FIGS. 1 and 2, and accordingly detailed explanations thereof will not be repeated hereunder.

The array type ultrasonic probe is constituted by arranging a plurality of rectangular piezoelectric elements 2 in an array on backing material 3 in a direction in which the short sides of respective piezoelectric elements 2 extend. FIG. 4 illustrates that a plurality of piezoelectric elements 2 are arranged in an array in a direction perpendicular to the drawing sheet. The upper and lower faces of piezoelectric element 2 consisting of a piezoelectric material are formed thereon with upper and lower face electrodes **1*a* and 1*b*. Metallic foils 6*a* and 6*b* bended in an L-shape are provided on opposite sides of the upper face of backing material 3, respectively. Between lower face electrode 1*b* and the upper face of backing material 3, first conductive adhesive 7 is interposed, so that piezoelectric element 2 is secured to backing material 3 and that lower face electrode 1*b* is electrically connected to metallic foils 6*a* and 6*b*, respectively, at the opposite sides of lower face electrode 1*b*. Second conductive adhesive 9 applied to the upper face and the side face of piezoelectric element 2 fixedly secures acoustic matching layer 4 to the upper face of piezoelectric element 2. Second conductive adhesive 9 is made to be integral with first conductive adhesive 7 on each of both side faces of piezoelectric element 2** so as to establish electric connection therebetween.

Further, in this array type probe, along one end portion of piezoelectric element 2, first slit 8 running from upper face electrode la to the upper portion of backing material 3 through piezoelectric element 2 is formed to be perpendicular to the major face of piezoelectric element 2 and to be parallel with the arranging direction of the plurality of piezoelectric elements 2. By this first slit 8, the piezoelectric material constituting piezoelectric elements 2 is separated so that the one end portion thereof is divided from the central portion and the other end portion thereof. Here, second conductive adhesive 9 is not separated by slit 8, and thus electrical connection between upper face electrodes **1*a* disposing on both sides of slit 8 can be acquired. Each of lower face electrode 1*b* and first conductive adhesive 7 are completely separated by first slit 8. Also, at the other end portion of piezoelectric element 2, second slit 10 running from the upper face of acoustic matching layer 4 to the upper portion of piezoelectric element 2 through second conductive adhesive 9 and upper face electrode 1***a* is formed to be perpendicular to the major face of piezoelectric element 2 and to be parallel with the arranging direction of the plurality of piezoelectric elements 2. Second slit 10 completely separates each of upper face electrode 1*a* and second conductive adhesive 9.

Thus, due to provision of two slits 8 and 10, metallic foil 6*a* is electrically connected to the major portion of lower face electrode 1*b* and upper face electrode 1*a* disposed on the other end portion of piezoelectric element 2, and metallic foil 6*b* is electrically connected to the major portion of upper face electrode 1*a* and lower face electrode 1*b* disposed on the one end portion of piezoelectric element 2.

A description of the manufacturing process of this array type ultrasonic probe will now be provided below.

First, a piece of plate-shape piezoelectric body having an extent thereof corresponding to that of a plurality of piezoelectric elements 2 of the array type probe is prepared, and on respective upper and lower faces of this piezoelectric body, upper face electrode 1*a* and lower face electrode 1*b* are formed. Further, a high electric voltage is applied between upper face electrode 1*a* and lower face electrode 1*b* to polarize the piezoelectric body. Furthermore, backing material 3 having an upper face thereof provided with metallic foils 6*a* and 6*b* disposed on opposite sides of the upper face is prepared. Metallic foils 6*a* and 6*b* have a length, respectively, which corresponds to the length of arrangement occupied by a plurality of piezoelectric elements 2.

Onto the upper face of such backing material 3, the piezoelectric body after polarization is fixedly secured by first conductive adhesive 7. As a result, the opposite sides of lower face electrode 1*b* of the piezoelectric plate are electrically connected to metallic foils 6*a* and 6*b*, respectively, by first conductive adhesive. Subsequently, at one end in the widthwise direction of the piezoelectric plate, first slit 8 is provided, which runs from upper face electrode 1*a* and reaches backing material 3, so that the piezoelectric plate together with lower face electrode 1*b* are separated.

Subsequently, on the upper face electrode 1*a* and the side faces of the piezoelectric plate, second conductive adhesive 9 is applied to fixedly secure acoustic matching layer 4 on upper face electrode 1*a*. In this step, acoustic matching layer 4 has a surface dimension substantially equal to that of the piezoelectric plate. At this stage, second conductive adhesive 9 is applied so as to be electrically connected to first conductive adhesive 7 including metallic foils 6*a* and 6*b*, and so as to electrically connect upper face electrodes la disposed on both sides of first slit 8. However, an amount of application of second conductive adhesive 9 should avoid becoming excessive in order to prevent second conductive adhesive from entering deep into first slit 8 thereby resulting in electrically short-circuiting between lower face electrodes 1*b* disposed on both sides of first slit 8. For this purpose, before the application of second conductive adhesive 9, suitable insulating filler may be poured in first slit 8. Then, at the other end in the widthwise direction of the piezoelectric plate, second slit 10 is provided, which runs from the upper face of acoustic matching layer 4 and reaches the piezoelectric plate, so as to divide upper face electrode 1*a*. Thereafter, suitable insulating filler may be poured in second slit 10.

Finally, apertures running from the upper face of acoustic matching layer 4 so as to reach backing material 3 and metallic foils 6*a* and 6*b*, and extending perpendicularly to a direction in which the plurality of piezoelectric elements 2 are arranged, are formed so as to separate the piezoelectric plate into the plurality of piezoelectric elements 2, as shown in FIG. 5. Furthermore, although metallic foil 6*b* on the one side is provided with apertures, it is entirely continuous, and is grounded to the earth potential. On the other hand, metallic foil 6*a* on the other side is separated into pieces for every piezoelectric element 2, and forms signal lines to which driving voltages for respective piezoelectric elements 2 is applied.

In the array type ultrasonic probe as described above, lower face electrode 1*b* of piezoelectric element 2 is separated by first slit 8 provided along the one end portion of the element, and upper face electrode 1*b* is separated by second slit 10 provided along the other end portion of the element. Further, at each of the opposite end portions of piezoelectric elements 2, upper face electrode 1*a* and lower face electrode 1*b* are electrically connected together by conductive adhesives 7 and 9. Therefore, since both electrodes 1*a* and 1*b* are kept to have an identical electrical potential at the opposite end portions of piezoelectric elements 2, ultrasonic wave is not radiated from the opposite end portions of piezoelectric elements 2 and is radiated from only the central region thereof in which acoustic matching layer 4 is arranged. Thus, any interference of ultrasonic waves caused by the radiation from the opposite end portions of piezoelectric elements 2 can be surely prevented, and a good acoustic field characteristic can be acquired. Furthermore, since this array type probe differing from the array type probe of the prior art as shown in FIG. 1, employs no lead wires 5*a* and 5*b* for the earthing, there occurs no adverse affect by dispersion of receiving signals.

In the above-described array type ultrasonic probe, since first and second slits 8 and 10 are formed in the piezoelectric plate after it is subjected to polarizing treatment, the width of slits 8 and 10 can be made the smallest. Therefore, spacing between first and second slits 8 and 10, namely, the effective length of each piezoelectric element 2 can be made large. Further, since first and second slits 8 and 10 may be arbitrarily formed so as to determine an effective length of piezoelectric element 2, it is possible to increase the degree of freedom of design. Furthermore, since the piezoelectric plate may be made to have common specifications, when an array type ultrasonic probe is manufactured in compliance with the specifications that a customer requests, it is possible to reduce the number of kinds of article to be prepared beforehand as a piezoelectric plate, and therefore producibility of the probe can be increased.

A description of an array type ultrasonic probe according to a second embodiment of the present invention will be provided hereinbelow.

Figure 6:
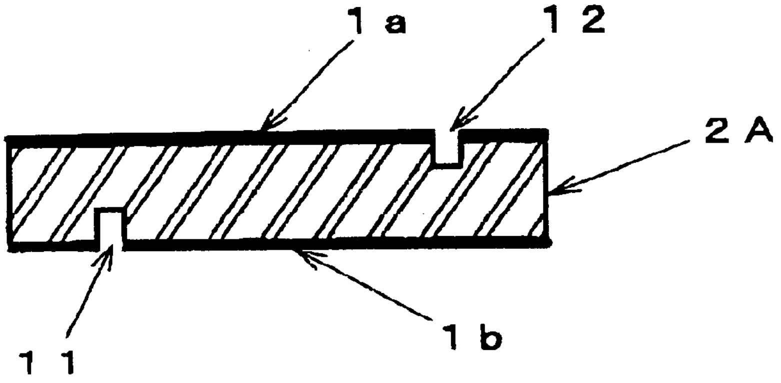
FIG. 6 is a cross-sectional view illustrating a piezoelectric plate used for an array type ultrasonic probe according to a second embodiment of the present invention.
Figure 7:
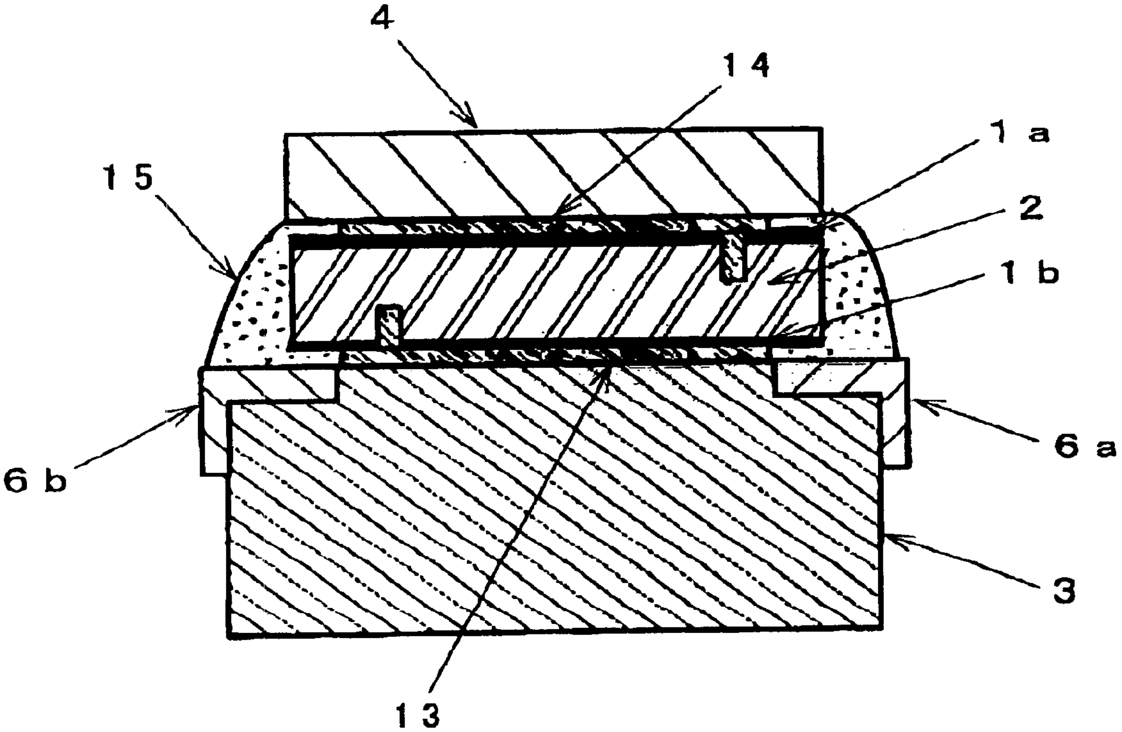
FIG. 7 is a cross-sectional view of the array type ultrasonic probe according to the second embodiment.

In the first embodiment, after securing a piezoelectric plate to a backing material, slits are formed. However, in the second embodiment, a piezoelectric plate preliminarily formed therein with grooves is prepared. In FIGS. 6 and 7 illustrating the array type ultrasonic probe according to the second embodiment, constituents designated by the same reference numerals as those in FIGS. 4 and 5 are the same as those shown in FIGS. 4 and 5, and therefore detailed description of those constituents will not be repeated again hereinbelow.

A piezoelectric plate 2A having an extent corresponding to a plurality of piezoelectric elements 2, formed thereon with upper face electrode 1*a* and lower face electrode 1*b*, and polarized beforehand is prepared. Then, as shown in FIG. 6, at a side portion of piezoelectric plate 2A, a groove

11 is provided for cutting lower face electrode 1*b* from the lower face of piezoelectric plate 2A, and at the other side portion of piezoelectric plate 2A, a groove 12 is provided for cutting upper face electrode 1*a* from the upper face of piezoelectric plate 2A. Grooves 11 and 12 are formed so as to extend in a direction in which piezoelectric elements 2 are arranged in an array.

Subsequently, similar to the first embodiment, backing material 3 provided with metallic foils 6*a* and 6*b* at opposite sides of the upper face thereof is prepared, and to a central region of the upper face of backing material 3, first insulating adhesive is applied so as to fixedly secure piezoelectric plate 2A onto backing material 3. Subsequently, to a central region of the upper face of piezoelectric plate 2A, second insulating adhesive is applied, and also conductive adhesive 15 is applied to a portion extending from the opposite side portions of the upper face to the side faces of piezoelectric plate 2A, so as to fixedly secure acoustic matching layer 4 onto piezoelectric plate 2A. At this time, upper face electrode 1*a* and lower face electrode 1*b* is electrically connected by conductive adhesive 15 to metallic foils 6*a* and 6*b*. Further, similar to the case of the first embodiment, an aperture running from the upper face of acoustic matching layer 4 and reaching backing material 3 and metallic foils 6*a* and 6*b* is provided so as to separate piezoelectric plate 2A into a plurality of piezoelectric elements 2. This aperture is provided so as to extend perpendicularly to a widthwise direction of piezoelectric plate 2A, namely a direction in which the plurality of piezoelectric elements 2 are to be arranged in an array.

By undergoing the above-described manufacturing process, an array type ultrasonic probe of which the cross-sectional construction is shown in FIG. 7 can be acquired. In this array type probe, lower and upper face electrodes 1*b* and 1*a* of piezoelectric element 2 are respectively separated by grooves 11 and 12 provided along both end portions of the piezoelectric element. At each of both end portions of piezoelectric element 2, upper and lower face electrodes 1*a* and 1*b* are electrically connected together by conductive adhesive 15. Therefore, in this array type probe, electrodes 1*a* and 1*b* are made to have an identical electric potential at both end portions of piezoelectric element 2, and no ultrasonic wave is radiated from both end portions of respective piezoelectric elements 2, and radiation of the ultrasonic wave occurs from only the central region thereof in which acoustic matching layer 4 is arranged. Thus, interference, which might occur if ultrasonic waves were radiated from both end portions of the piezoelectric element, can be prevented resulting in obtaining a good acoustic field characteristic. Further, in this array type probe differing from the ultrasonic probe of the prior art as shown in FIG. 1, since no lead wires 5*a* and 5*b* are employed, and accordingly there occurs no adverse affect due to dispersion of receiving signals.

Furthermore, since polarization of piezoelectric plate 2A is completed before the formation of grooves 11 and 12, width of each of grooves 11 and 12 may be made the smallest, similarly to the case of the first embodiment. Therefore, according to this embodiment, spacing between first and second grooves 11 and 12, namely an effective length of each of piezoelectric elements 2 may be made large, and the effective length per se may be arbitrarily set so as to increase a degree of freedom of design. Also, piezoelectric plate 2A may be made to have common specifications, and accordingly it is possible to reduce the number of kinds of article to be prepared beforehand as a piezoelectric plate to thereby permit it to increase producibility of this array type ultrasonic probe.

Although the description of the preferred embodiments of the present invention has been provided, it should be understood that the present invention should not be limited to the above-described embodiments. For example, metallic foils 6*a* and 6*b* may not be provided on backing material 3 beforehand, and these foils may be preliminarily connected to the opposite sides of the lower face of the piezoelectric body, respectively, by the use of a solder or the like.

Figure 8:
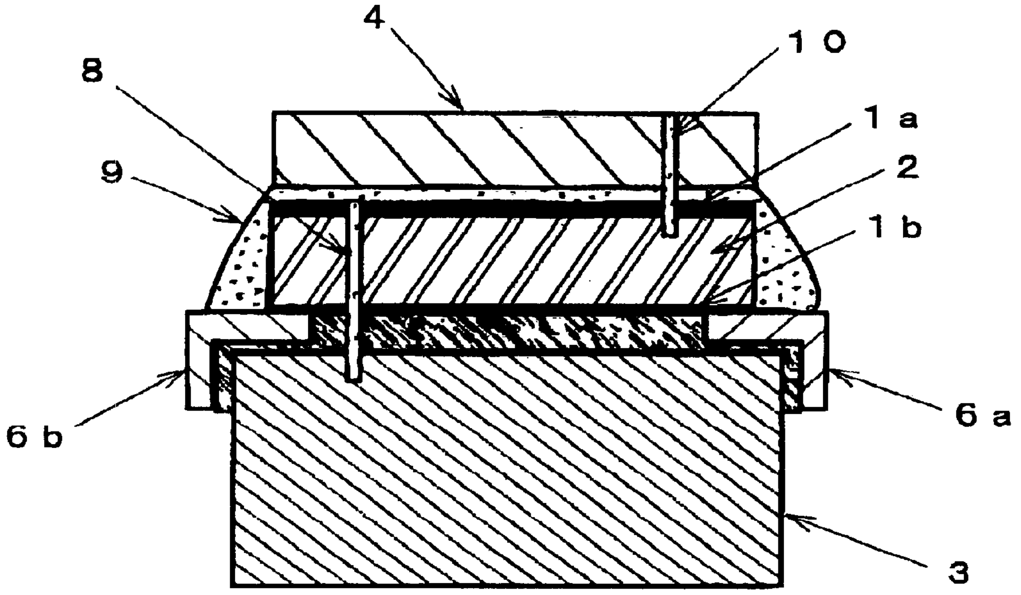
FIG. 8 is a cross-sectional view of the array type ultrasonic probe according to a further embodiment of the present invention; and, FIG. 9 is cross-sectional view of the array type ultrasonic probe according to a still further embodiment of the present invention.

FIG. 8 illustrates a cross-sectional construction of an array type probe obtained when, in the first embodiment, a piezoelectric body provided with metallic foils 6*a* and 6*b* provided on both sides of the lower face thereof is used. This ultrasonic probe is produced as described below. Namely, after metallic foils 6*a* and 6*b* are beforehand connected, by soldering or the like, to the opposite sides of the lower face of a plate-like piezoelectric body, the piezoelectric body is fixed to backing material 3 by either insulating adhesive or an adhesive double coated insulating tape. Then, first slit 8 is provided, and insulating filler is poured into the slit. Thereafter, acoustic matching layer 4 is fixedly secured to the upper face of the piezoelectric body, and upper and lower face electrodes 1*a* and 1*b* are connected to metallic foils 6*a* and 6*b*, both by the use of conductive adhesive 9. Then, second slit 10 running from the upper face of acoustic matching layer 4 and reaching the piezoelectric body is provided, and insulating filler is poured into second slit 10. Further, similarly to the manner described with the first embodiment, the piezoelectric body is separated into individual piezoelectric elements 2 so as to acquire the array type probe.

Similarly, in the second embodiment, metallic foils 6*a* and 6*b* can be beforehand connected to the opposite sides of the lower face of a piezoelectric body.

Figure 9:
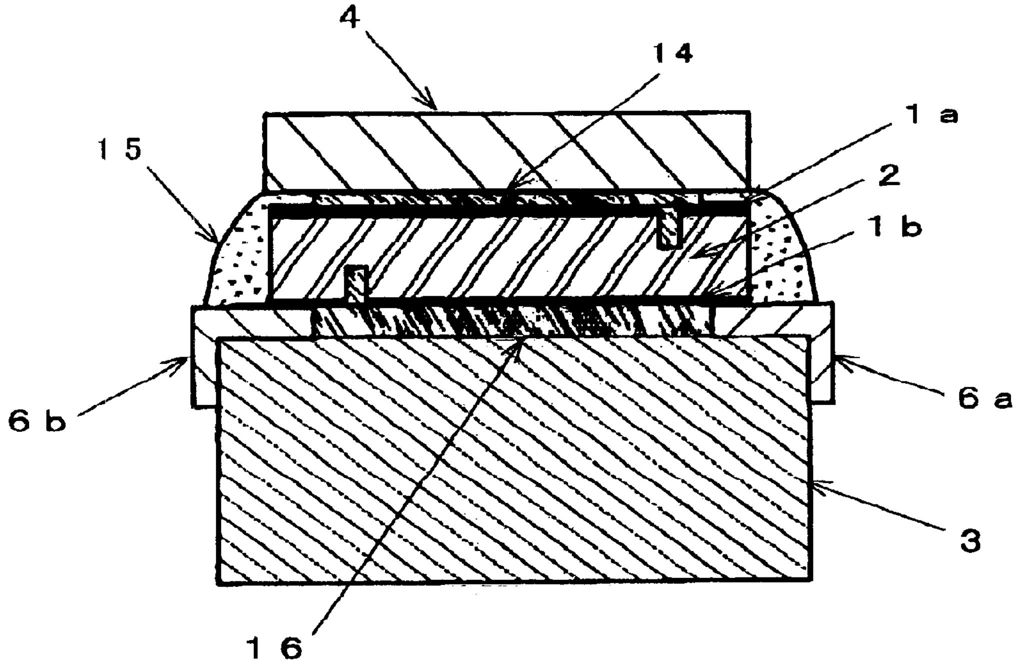

FIG. 9 illustrates a cross-sectional construction of an ultrasonic probe obtained when, in the second embodiment, a piezoelectric body provided with metallic foils 6*a* and 6*b* provided on both side portions of the lower face thereof is used. In this case, a piezoelectric body to which metallic foils 6*a* and 6*b* are beforehand connected, and provided with grooves 11 and 12 beforehand formed therein is fixedly secured onto backing material 3 by insulating adhesive 16. Then, the process similar to that of the second embodiment may complete production of the array type probe.

Further, in the second embodiment, although first and second grooves are formed in the lower and upper faces of the piezoelectric body, respectively, for example, a piezoelectric body formed with a groove in only the lower face thereof may be used, and this piezoelectric body may be fixedly secured to-the upper face of backing material 3. Then, on the upper face of the piezoelectric body, acoustic matching layer is provided, and thereafter similar to the second slit of the first embodiment, a slit running from the upper face of the acoustic matching layer and reaching the upper portion of the piezoelectric body may be formed so as to divide the upper face electrode.

Furthermore, means for mutually electrically connecting the upper and lower face electrodes at the opposite end portions of the piezoelectric elements is not limited to only conductive adhesive, but metallic plating and other conductive material, which are capable of electrically and mutually connecting both electrodes, may be used if both electrodes were successfully electrically connected by such measures. Further, in the respective illustration of the drawings, the matching layer is shown as a single layer. However, a matching layer having such a construction that plural layers are laminated together, may be used. The surface of the piezoelectric elements is not needed to be flat, and for example, the surface may be formed in a concaved face.

While preferred embodiments of the present invention have been described using specific terms, such description is for illustrative purpose only, and it is to be understood that changes and variations may occur to a person skilled in the art without departing from the spirit or scope of the following claims.

What is claimed is:

1. An array type ultrasonic probe comprising:

a backing material;

a plurality of piezoelectric elements arranged on and fixedly secured to said backing material, each said piezoelectric element having a first end portion, a second end portion opposing said first end portion, a first major face facing said backing material, a second major face, a lower face electrode formed on said first major face, and an upper face electrode formed on said second major face;

a first conductive member for electrically connecting said lower face electrode and said upper face electrode at said first end portion; and a second conductive member for electrically connecting said lower face electrode and said upper face electrode at said second end portion;

wherein said first major face is formed, along said first end portion, with a first notch portion to thereby electrically separate said lower face electrode, and said second major face is formed, along said second end portion, with a second notch portion to thereby electrically separate said upper face electrode.

2. The array type ultrasonic probe according to claim 1, wherein said first and second notch portions extend in a direction in which said plurality of piezoelectric elements are arranged in an array.

3. The array type ultrasonic probe according to claim 1, wherein said second major face has further thereon an acoustic matching layer.

4. The array type ultrasonic probe according to claim 3, wherein said first notch portion comprises a first slit which separates said lower face electrode and reaches said second major face to thereby separate a piezoelectric material of said piezoelectric element, and said second notch portion comprises a second slit which reaches a piezoelectric body of said piezoelectric element from an upper face of said acoustic matching layer to thereby cut said second major face.

5. The array type ultrasonic probe according to claim 3, wherein said first notch portion comprises a first groove formed in said first major face, and said second notch portion comprises a second groove formed in said second major face.

6. The array type ultrasonic probe according to claim 4, wherein said first and second conductive members comprise conductive adhesive.

7. The array type ultrasonic probe according to claim 5, wherein said first and second conductive members comprise conductive adhesive.

8. The array type ultrasonic probe according to claim 6, further comprising first and second metallic foils for leading said first and second conductive members out, respectively.

9. The array type ultrasonic probe according to claim 7, further comprising first and second metallic foils for leading said first and second conductive members out, respectively.

10. The array type ultrasonic probe according to claim 6, wherein said piezoelectric element is secured on said backing material by said conductive adhesive and said acoustic matching layer is secured on said piezoelectric element by said conductive adhesive.

11. The array type ultrasonic probe according to claim 6, wherein said piezoelectric element is secured on said backing material by insulating adhesive and said acoustic matching layer is secured on said piezoelectric element by the insulating adhesive.

12. A manufacturing method of an array type ultrasonic probe including a backing material and a plurality of piezoelectric elements arranged on said backing material, comprising the steps of:

fixedly securing a piezoelectric plate formed thereon with an upper face electrode and a lower face electrode to said backing material by a first conductive adhesive so that said lower face electrode faces said backing material;

forming a first slit running from said upper face electrode to said backing material, relative to a first side of said piezoelectric plate;

fixedly securing an acoustic matching layer onto said upper face electrode by a second conductive adhesive while electrically connecting said upper and lower face electrodes by said second adhesive at said first side and a second side of said piezoelectric plate, said second side opposing said first side;

forming a second slit running from an upper face of said acoustic matching layer to said piezoelectric plate while separating said upper face electrode, relative to said second side of said piezoelectric plate; and thereafter separating said piezoelectric plate into individual piezoelectric elements.

13. A manufacturing method of an array type ultrasonic probe including a backing material and a plurality of piezoelectric elements arranged on said backing material, comprising the steps of:

fixedly securing a piezoelectric plate formed with upper and lower face electrodes together with a first groove separating said lower face electrode on a first side of said piezoelectric plate, and a second groove separating said upper face electrode on a second side of said piezoelectric plate, to said backing material in a manner such that said lower face electrode faces said backing member, by applying insulating adhesive to a central region of said backing material, said second side opposing said first side;

applying insulating adhesive to a central region of said upper face electrode and conductive adhesive to side regions of said upper face electrode to thereby fixedly secure an acoustic matching layer onto said upper face electrode while electrically connecting said upper and lower face electrodes by said conductive adhesive at said first and second sides of said piezoelectric plate; and thereafter separating said piezoelectric plate into individual piezoelectric elements.

* * * * *